US008463362B2

(12) United States Patent
Fago

(10) Patent No.: US 8,463,362 B2
(45) Date of Patent: Jun. 11, 2013

(54) MULTI-DOSE INJECTION SYSTEM

(75) Inventor: Frank M. Fago, Mason, OH (US)

(73) Assignee: Mallinckrodt LLC, Hazelwood, MO (US)

( * ) Notice: Subject to any disclaimer, the term of this patent is extended or adjusted under 35 U.S.C. 154(b) by 27 days.

(21) Appl. No.: 13/126,210

(22) PCT Filed: Oct. 22, 2009

(86) PCT No.: PCT/US2009/061568
§ 371 (c)(1),
(2), (4) Date: Apr. 27, 2011

(87) PCT Pub. No.: WO2010/051205
PCT Pub. Date: May 6, 2010

(65) Prior Publication Data
US 2011/0208047 A1     Aug. 25, 2011

Related U.S. Application Data

(60) Provisional application No. 61/109,964, filed on Oct. 31, 2008.

(51) Int. Cl.
A61B 6/00      (2006.01)
A61B 5/055     (2006.01)
A61M 25/16     (2006.01)

(52) U.S. Cl.
USPC ............................ 600/432; 600/420; 604/533

(58) Field of Classification Search
USPC ... 600/420, 431, 432; 604/533, 403; 424/1.11
See application file for complete search history.

(56) References Cited

U.S. PATENT DOCUMENTS

| 6,170,758 | B1 | 1/2001 | Lee |
| 2004/0199075 | A1 | 10/2004 | Evans, III et al. |
| 2005/0004447 | A1 | 1/2005 | Yamamoto |
| 2007/0161970 | A1 | 7/2007 | Spohn et al. |
| 2008/0131362 | A1 | 6/2008 | Rousso et al. |

FOREIGN PATENT DOCUMENTS

| EP | 0170009 | 2/1986 |
| EP | 1361456 | 11/2003 |
| EP | 1618907 | 1/2006 |

Primary Examiner — Michael Rozanski
(74) Attorney, Agent, or Firm — Marsh, Fischmann, & Breyfogle LLP

(57) ABSTRACT

A multi-dose injection system (108) is disclosed that allows for safe and easy use of bulk containers, a multi-use tubing set (110), and syringes (86a, 86b) across multiple patients. The bulk containers may include a saline bottle (118) and a contrast bottle (120) for administration to a series of patients undergoing imaging procedures. The bottles (118, 120) may be fluidly connected to a cassette (114) that includes a saline valve (176) and a contrast valve (178) operable to control flow from the saline bottle (118) and the contrast bottle (120), respectively. The cassette (114) may be fluidly interconnected to the multi-use tubing set (110) that is, in turn, fluidly connected to syringes (86a, 86b) on a powerhead (50) and a patient-specific tubing set (112). The patient-specific tubing set (112) may be replaced between patients and may also serve to isolate the remainder of the multi-dose injection system (108) from contamination from bodily fluids.

34 Claims, 9 Drawing Sheets

MULTI-DOSE INJECTION SYSTEM

RELATED APPLICATIONS

This application is a U.S. National Stage of PCT/US2009/0061568 filed on 22 Oct. 2009, which claims priority to and is a non-provisional application of U.S. provisional application Ser. No. 61/109,964 filed on 31 Oct. 2008 entitled "Multi-Dose Injection System". Priority is claimed to each patent application set forth in this Related Applications section.

FIELD OF THE INVENTION

The present invention generally relates to injection systems and, more particularly, to injection systems and methods to deliver multiple doses of fluids into one or more patients.

BACKGROUND

Various medical procedures require that one or more medical fluids be injected into a patient. For example, medical imaging procedures oftentimes involve the injection of contrast media into a patient, possibly along with saline and/or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

One way to categorize syringes used by power injectors is the manner in which they are filled or loaded with fluid. Power injector syringes may be pre-filled—syringes that are filled with fluid at one facility and then shipped to another facility (e.g., an end-use facility). Empty syringes may be shipped to the end-use facility, and may then be filled with fluid in at least two general manners. An empty syringe may be filled with fluid at one location within the end-use facility (e.g., at a filling station), and then transferred to another location within the end-use facility (e.g., an imaging suite) where the fluid-containing syringe is then installed on a power injector. Alternatively, an empty syringe may be installed on a power injector at the end-use facility (e.g., in an imaging suite) and then loaded or filled with fluid in preparation for a subsequent injection protocol using the power injector and the installed syringe.

Typically, an individual empty syringe may be filled in accordance with the foregoing from what may be characterized as a bulk supply container (e.g., bottle). In this case, the syringe is used for a single injection on a single patient. Any contrast media remaining in the syringe after this single injection cannot be used for another patient and is thereby wasted. Moreover, the entire tubing set extending from the power injector to the patient (including the various components that may be incorporated into the tubing set, such as one or more valves and a catheter) is also discarded.

SUMMARY

First through third aspects of the present invention are each embodied by a multi-dose injection system. The multi-dose injection system of these three aspects includes an injection device (e.g., a power injector), a bulk fluid container holder module, a cassette, and a tubing set. This multi-dose injection system is operable to transfer fluid from one or more bulk fluid containers disposed within the bulk fluid container holder module, to the injection device (e.g., a syringe thereof) and then to a patient fluidly interconnected to the tubing set. As used herein, the term "fluidly interconnected" refers to two or more components or entities being connected (either directly or indirectly) in a manner such that fluid is capable of flowing (e.g., unidirectionally or bidirectionally) therebetween. For example, "an injection device fluidly interconnected to a patient" describes a configuration where fluid can flow from the injection device through any interconnecting devices (e.g., tubing, connectors) and into the patient.

In the case of the first aspect, the bulk fluid container holder module of the multi-dose injection system includes container holders (i.e., more than one container holder). Each of these container holders is adapted to receive a separate bulk fluid container (e.g., a saline container, a contrast media container). The cassette is detachably interconnected with the bulk fluid container holder module and includes bulk fluid container fluid interfaces. Each of these bulk fluid container fluid interfaces of the cassette is associated with a separate one of the container holders. The tubing set of the multi-dose injection system is fluidly interconnected to the injection device and the bulk fluid container fluid interfaces of the cassette.

In the case of the multi-dose injection system of the second aspect, the cassette includes a bulk fluid container fluid interface and a valve. The cassette is detachably interconnected to the bulk fluid container holder module. The tubing set is fluidly interconnected to the injection device and the cassette, and the valve is operable to fluidly isolate the bulk fluid container fluid interface from the tubing set. In some embodiments, the bulk fluid container holder module may include a plurality of container holders (e.g., a saline container holder and a contrast media container holder). As used herein, the term "fluidly isolated" describes a relationship between components or entities where fluid is at least temporarily precluded from flowing between the components or entities. For example, "a bulk fluid container fluid interface fluidly isolated from a tubing set" describes a configuration where fluid located at the bulk fluid container fluid interface is at least temporarily precluded from flowing from the bulk fluid container fluid interface to the tubing set. Such inability to flow may be because no interconnecting devices connect the bulk fluid container fluid interface and the tubing set or because a device, such as a closed valve, prevents flow from the bulk fluid container fluid interface to the tubing set.

In the case of the multi-dose injection system of the third aspect, the bulk fluid container holder module includes a plurality of container holders (e.g., a saline container holder and a contrast media container holder). Each of these container holders is operable to cradle a corresponding bulk fluid container. The bulk fluid container holder module also includes a heating member operable to generate heat and transfer the generated heat to one or more bulk fluid containers disposed within the bulk fluid container holder. The cassette includes a bulk fluid container fluid interface and a valve. The tubing set is fluidly interconnected to the injection device and the cassette. In some embodiments, the cassette may be detachably interconnected to the bulk fluid container holder module. As used herein, the term "detachably interconnected" describes a relationship between components where the components are interconnected yet retain the ability to be detached from each other where, after detaching, at least one of the components remains in a usable condition. For example, "the cassette and bulk fluid container holder module are detachably interconnected" describes a condition where the cassette is currently interconnected with the bulk fluid container holder module in a manner that allows for the cassette to be detached from the bulk fluid container holder module. Furthermore, after such detaching, at least one of the bulk fluid container holder module and the cassette retains the ability to be interconnected (e.g., detachably) with another component.

A number of feature refinements and additional features are separately applicable in relation to each of the above-noted first, second, and third aspects of the present invention. These feature refinements and additional features may be used individually or in any combination in relation to each of the first, second, and third aspects. That is, each of the following features that will be discussed is not required to be used with any other feature or combination of features unless otherwise specified.

The bulk fluid container holder module may include a bulk fluid container heater. This bulk fluid container heater may be of any appropriate size, shape, configuration, and/or type. In some embodiments, a separate bulk fluid container heater may be provided for each container holder of the bulk fluid container holder module. In other embodiments, a single bulk fluid container heater could be provided for multiple (e.g., all) container holders of the bulk fluid container holder module. In yet other embodiments, a first bulk fluid container heater could be provided for one or more container holders of the bulk fluid container holder module, and a second bulk fluid container heater could be provided for one or more different container holders of the bulk fluid container holder module.

In multi-dose injection systems that include a plurality of container holders, the cassette may include a separate bulk fluid container fluid interface and a valve for each one of the container holders. Each valve may be disposed within a housing of the cassette and/or may be operable to fluidly isolate its corresponding bulk fluid container fluid interface from the tubing set.

The cassette may include a bulk fluid container fluid interface and a valve for each included container holder. In such cassettes, each bulk fluid container fluid interface may include a vented spike that may exhibit any appropriate design. For instance, the vented spike may extend into an interior of a housing of the cassette. In such embodiments, the tubing set may be fluidly interconnected to each vented spike within the interior of the housing.

The bulk fluid container holder module may include a valve actuator for each valve of the cassette. Each of the valve actuators may be operable to open and close in synchronization with movement of one or more components of the injection device (e.g., movement of a plunger of a syringe that is located within and movable relative to a barrel of the syringe). A position of one or more (e.g., each) of the valve actuators may be electronically controllable.

In some embodiments of the multi-dose injection system, the cassette and the tubing set may be permanently connected to each other. In other words, the cassette and the tubing set may be provided in a manner such that they are effectively a single, unitary component. In this regard, the cassette and tubing set may be intended to be installed and replaced as a single unit. In other embodiments, the cassette and the tubing set may be designed to be removably connected to each other. In other words, the cassette and the tubing set may be provided in a manner such that each is a discrete component that is meant to be connected and disconnected with the other as desired by a user. In this regard, a decision to use, reuse, and/or replace a given one of the cassette and tubing set would be substantially independent of a decision to use, reuse, and/or replace the other.

Some embodiments of the first, second, and third aspects may include a patient-specific tubing set that may be fluidly interconnected to the tubing set. This patient-specific tubing set may include one end (e.g., opposite an end that is fluidly interconnected to the tubing set) designed to be fluidly interconnected to a catheter configured to be insertable into the vasculature of a patient. The patient-specific tubing set may be replaced each time a new patient is to receive an injection of fluids from the multi-dose injection system.

Multi-dose injection systems of the first, second, and third aspects may include a cassette identification reader capable of reading a cassette identification member of the cassette. Such a reader may be an electromagnetic device capable of electromagnetically reading data from and/or writing data to an appropriate data tag (e.g., read and/or writing data to a Radio Frequency Identification (RFID) tag via appropriate radiofrequency). Accordingly, the cassette identification member may be an RFID tag. Additionally or alternatively, multi-dose injection systems of the first, second, and third aspects may include one or more bulk fluid container identification readers capable of reading one or more bulk fluid container identification members connected to one or more bulk fluid containers. Such bulk fluid container identification readers may be electromagnetic devices capable of electromagnetically reading data from and/or writing data to appropriate data tags. Accordingly, the bulk fluid container identification members may be RFID tags. In embodiments where both a cassette identification reader and one or more bulk fluid container identification readers are present, each of the readers may be a discrete reader, or a single reader may be utilized to perform the functions of both the cassette identification reader and the bulk fluid container identification reader(s) (i.e., a single reader would read both cassette identification members and bulk fluid container identification members).

A fourth aspect of the present invention is embodied by a method of delivering a medical fluid to the vasculature (e.g., artery, vein, etc.) of a patient. The method may comprise installing a cassette on a bulk fluid container holder module, fluidly attaching a multi-use tubing set to an injection device, fluidly interconnecting a first patient-specific tubing set to the multi-use tubing set, and fluidly connecting a first bulk fluid container to a first bulk fluid container fluid interface of the cassette. The method may further include after the installing, fluidly attaching, fluidly interconnecting, and fluidly connecting steps, actuating a first valve of the cassette to place the first bulk fluid container in fluid communication with the multi-use tubing set. The method may further include performing a fluid transfer sequence. The fluid transfer sequence may comprise retracting a plunger of the injection device while the first bulk fluid container is in fluid communication with the multi-use tubing set, resulting in fluid moving from the first bulk fluid container into a syringe of the injection device, then closing the first valve, and then advancing the plunger to expel fluid from the syringe into the multi-dose tubing set, through the first patient-specific tubing set, and into the vasculature of the patient.

A number of feature refinements and additional features are separately applicable in relation to the above-noted fourth aspect of the present invention. These feature refinements and additional features may be used individually or in any combination in relation to the fourth aspect. That is, each of the following features that will be discussed are not required to be used with any other feature or combination of features unless otherwise specified.

In an embodiment, the method of delivering a medical fluid to the vasculature of a patient may include fluidly connecting a second bulk fluid container to a second bulk fluid container fluid interface of the cassette. In an embodiment, the method may include fluidly connecting any appropriate number of bulk fluid containers to corresponding bulk fluid container fluid interfaces of the cassette. In an exemplary configuration, the first bulk fluid container may comprise saline and the second bulk fluid container may comprise contrast.

In an embodiment, the method may further include heating a fluid contained in the first bulk fluid container and/or heating a fluid in any other bulk fluid container used in the performance of the method.

Prior to the actuating step, an embodiment of the method may comprise reading an identification member attached to the cassette. The reading may comprise reading an RFID tag of the cassette with an RFID tag reader. The RFID tag reader may be integrated into the bulk fluid container holder module. Reading the RFID tag may, for example, enable identification of the type of cassette, the serial number of the cassette, and/or any other appropriate information regarding the cassette.

Prior to the actuating step, the method may comprise reading an identification member attached to the first bulk fluid container. The reading may comprise reading an RFID tag of the first bulk fluid container with an RFID tag reader. The RFID tag reader may be integrated into the bulk fluid container holder module. Reading the RFID tag may, for example, enable identification of the type of fluid within the first bulk fluid container, the volume of fluid within the first bulk fluid container, the serial number of the first bulk fluid container, and/or any other appropriate information regarding the first bulk fluid container. The RFID tag reader and/or additional RFID tag readers may be operable to read any additional bulk fluid containers that may held by the bulk fluid container holder module (e.g., to read the concentration of contrast stored with a given bulk fluid container).

In an embodiment of the method, the first bulk fluid container fluid interface may comprise a vented spike mounted to the cassette, and the fluidly connecting step may comprise pressing the first bulk fluid container onto the vented spike.

In an embodiment, the method may further comprise disconnecting the first patient-specific tubing set from the multi-use tubing set after the performing step, then fluidly joining a second patient-specific tubing set to the multi-use tubing set, and repeating the performing the fluid transfer sequence using the second patient-specific tubing set to deliver fluid into a vasculature of a second patient. Furthermore, the method may comprise maintaining a position of the plunger between the disconnecting and joining steps, and positioning, during the maintaining step, the first valve such that the first bulk fluid container may be in fluid communication with the multi-use tubing set, thereby preventing any pressure build up in the syringe. The disconnecting may occur at an interface of a female Luer connector of the multi-use tubing set and a first male Luer connector of the first patient-specific tubing set and the joining may occur at an interface of the female Luer connector and a second male Luer connector of the second patient-specific tubing set. The method may further comprise cleaning the female Luer connector after the disconnecting step and prior to the joining step. Such cleaning may include swabbing the female Luer connector (e.g., with an alcohol swab).

A number of feature refinements and additional features are separately applicable to each of above-noted first, second, third, and fourth aspects of the present invention. These feature refinements and additional features may be used individually or in any combination in relation to each of the above-noted first, second, third, and fourth aspects. Any feature of any other various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a power injector includes "a syringe" alone does not mean that the power injector includes only a single syringe). Moreover, any failure to use phrases such as "at least one" also does not limit the corresponding feature to the singular (e.g., indicating that a power injector includes "a syringe" alone does not mean that the power injector includes only a single syringe). Finally, use of the phrase "at least generally" or the like in relation to a particular feature encompasses the corresponding characteristic and insubstantial variations thereof (e.g., indicating that a syringe barrel is at least generally cylindrical encompasses the syringe barrel being cylindrical).

The injection device may be in the form of a power injector. Any such power injector that may be utilized to provide a fluid discharge may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading and/or drawing of fluid and/or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more drive sources of any appropriate size, shape, configuration, and/or type. Multiple drive source outputs may be combined in any appropriate manner to advance a single syringe plunger at a given time. One or more drive sources may be dedicated to a single syringe plunger driver, one or more drive sources may be associated with multiple syringe plunger drivers (e.g., incorporating a transmission of sorts to change the output from one syringe plunger to another syringe plunger), or a combination thereof. Representative drive source forms include a brushed or brushless electric motor, a hydraulic motor, a pneumatic motor, a piezoelectric motor, or a stepper motor.

Any such power injector may be used for any appropriate application where the delivery of one or more medical fluids is desired, including without limitation any appropriate medical application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging). Any such power injector may be used in conjunction with any component or combination of components, such as an appropriate imaging system (e.g., a CT scanner). For instance, information could be conveyed between any such power injector and one or more other components (e.g., scan delay information, injection start signal, injection rate).

Any appropriate number of syringes may be utilized with any such power injector in any appropriate manner (e.g., detachably; front-loaded; rear-loaded; side-loaded), any appropriate medical fluid may be discharged from a given syringe of any such power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit (e.g., a medical tubing set), where this conduit is fluidly interconnected with the syringe in any appropriate manner and directs fluid to a desired location (e.g., to a catheter that is inserted into a patient for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injectors syringe plunger drive assembly such that the syringe plunger drive assembly is able to advance the plunger in at least one direction, and possibly in two different, opposite directions.

Any multi-dose injection system or injection may include/utilize any number of bulk containers of fluid. Such multi-dose injection systems or injections may be used to deliver fluids from the bulk containers to multiple patients. The bulk containers may contain any appropriate type of fluid. The bulk containers may each contain a unique type of fluid or some or all of the bulk containers may contain the same type of fluid. The bulk containers may be fluidly interconnected to the multi-dose injection system via any appropriate number of valves. The bulk containers may be fluidly interconnected to any appropriate number of syringes.

DETAILED DESCRIPTION

Figure 1:
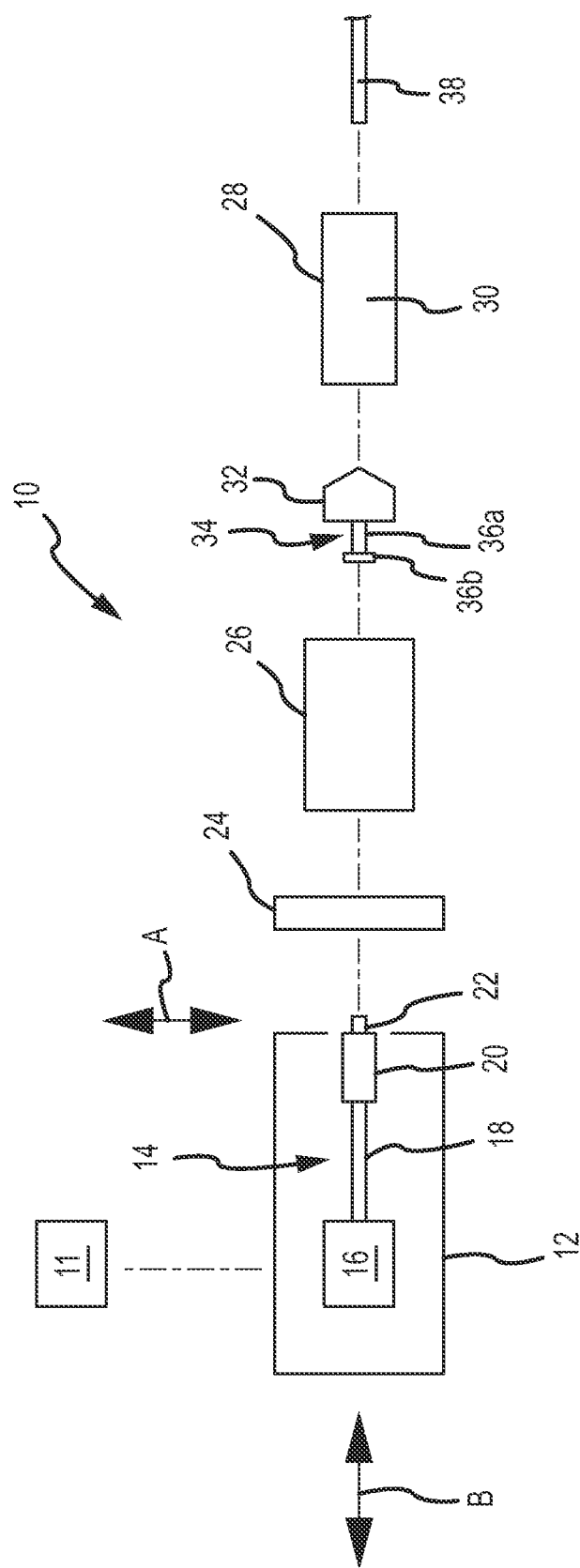
FIG. 1 is a schematic of one embodiment of a power injector.

FIG. 1 presents a schematic of one embodiment of an injection device in the form of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide any of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at feast some respect in relation to their respective functionalities.

A syringe 28 may be installed on the powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes the plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g., in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, these components may or may not be coupled when the ram 20 advances the syringe plunger 32 to discharge fluid from the syringe 28 (e.g., the ram 20 may simply "push on" the syringe plunger coupler 34 or on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
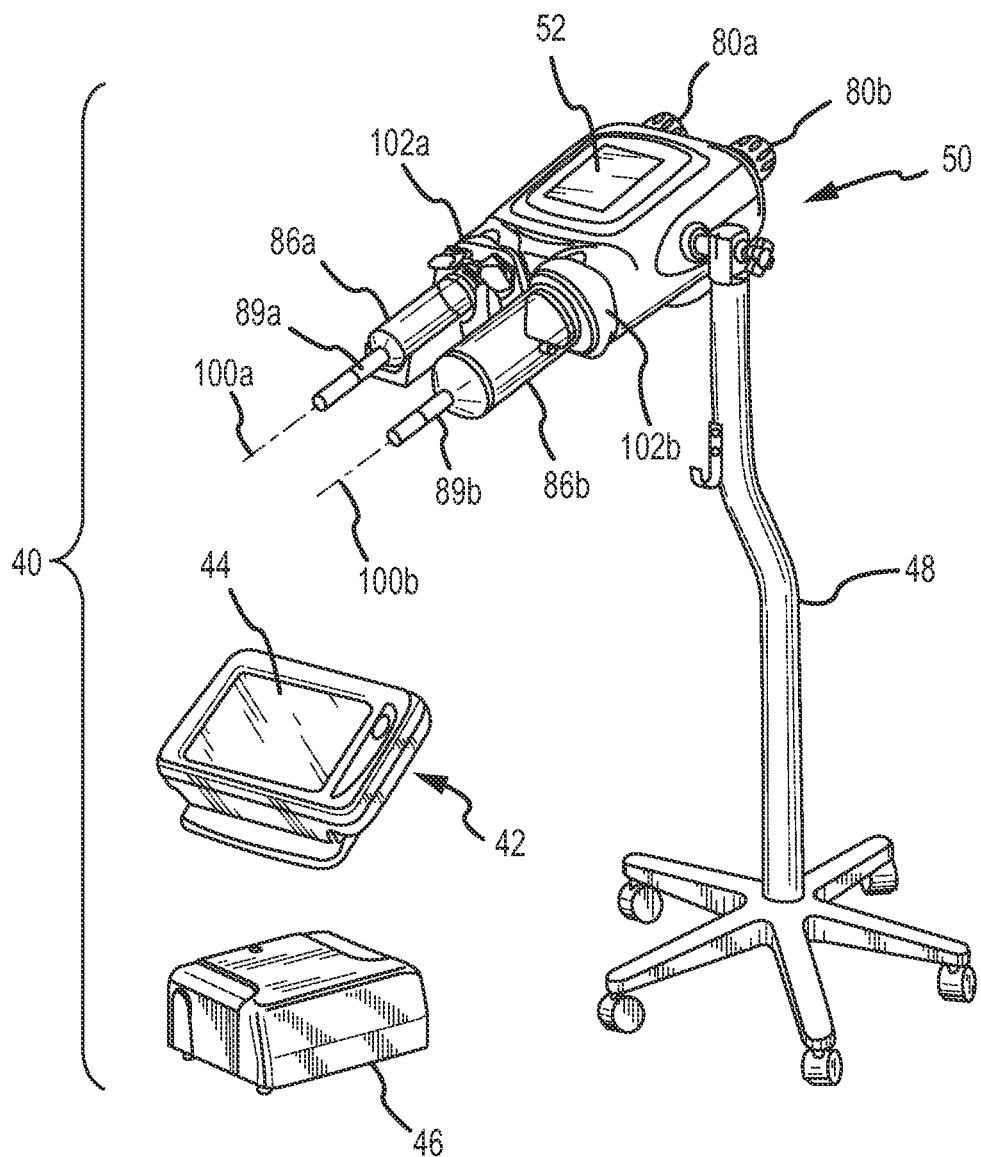
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 are mounted on the powerhead 50. Fluid may be drawn into and/or discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading or drawing fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at feast some respect (e.g., by having one or more support sections that may be repositioned relative to one or more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
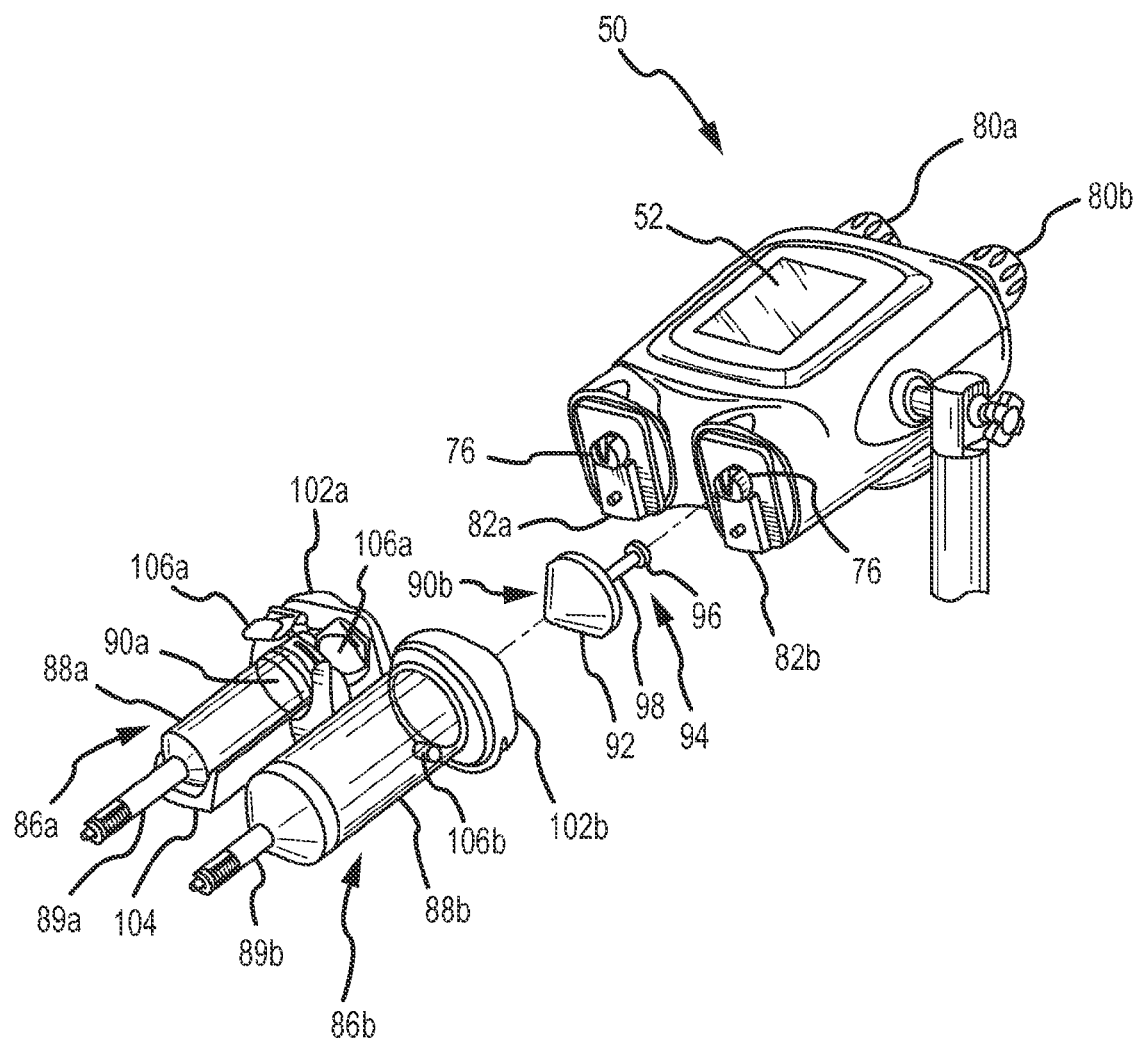
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within the syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b in a first direction along an axis 100b (FIG. 2A) via operation of the powerhead 50 will discharge fluid from within the syringe barrel 88b through a nozzle 89b of the syringe 86b. Movement of the plunger 90b in a direction opposite from the first direction along axis 100b (FIG. 2A) via operation of the powerhead 50 may, where the powerhead 50 is fluidly interconnected to a source of fluid, load fluid into the syringe barrel 88b through the nozzle 89b of the syringe 86b. An appropriate conduit (not shown) will typically be fluidly interconnected with the nozzle 89b in any appropriate manner to direct fluid to a desired location (e.g., a patient) and/or load fluid from a desired location (e.g., a fluid container).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74 (FIG. 2C), which are each part of a syringe plunger drive assembly or syringe plunger driver 56 (FIG. 2C) for the syringe 86a, is positioned in proximity to the faceplate 102a when mounted on the powerhead 50. Details regarding the syringe plunger drive assembly 56 will be discussed in more detail below in relation to FIG. 2C. Generally, the ram coupler 76 may be coupled with the syringe plunger 90a of the syringe 86a, and the ram coupler 76 and ram 74 (FIG. 2C) may then be moved relative to the powerhead 50 to move the syringe plunger 90a along the axis 100a (FIG. 2A). It may be such that the ram coupler 76 is engaged with, but not actually coupled to, the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 86a at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 far interfacing with the faceplate 102b. A ram coupler 76 of a ram 74 (FIG. 2C), which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 2C. Generally, the ram coupler 76 may be coupled with the syringe plunger 90b of the syringe 86b, and the ram coupler 76 and ram 74 (FIG. 2O) may be moved relative to the powerhead 50 to move the syringe plunger 90b along the axis 100b (FIG. 2A). It may be such that the ram coupler 76 is engaged with, but not actually coupled to, the syringe plunger 90b when moving the syringe plunger 90b to discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102b on and remove the faceplate 102b from its mounting 82b on the powerhead 50. The faceplate 102b also may be used to couple the syringe plunger 90b with its corresponding ram coupler 76 on the powerhead 50. In this regard, the faceplate 102b may include a handle 106b. Generally and with the syringe 86b being initially positioned within the faceplate 102b, the syringe 86b may be rotated along its long axis 100b (FIG. 2A) and relative to the faceplate 102b. This rotation may be realized by moving the handle 108b, by grasping and turning the syringe 86b, or both. In any case, this rotation moves/translates both the syringe 86b and the faceplate 102b at least generally within a plane that is orthogonal to the axes 100a, 100b (associated with movement of the syringe plungers 90a, 90b, respectively, and illustrated in FIG. 2A). Rotating the syringe 86b in one direction moves/translates the syringe 86b and faceplate 102b in an at least generally downward direction to couple the syringe plunger 90b with its corresponding ram coupler 76. Rotating the syringe 86b in the opposite direction moves/translates the syringe 86b and faceplate 102b in an at least generally upward direction to uncouple its syringe plunger 90b from its corresponding ram coupler 76.

As illustrated in FIG. 2B, the syringe plunger 90b includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90b and its corresponding ram coupler 76 are in a coupled state or condition. The syringe plunger 90a may include a similar syringe plunger coupler 94 for interfacing with its corresponding ram coupler 76.

Figure 2C:
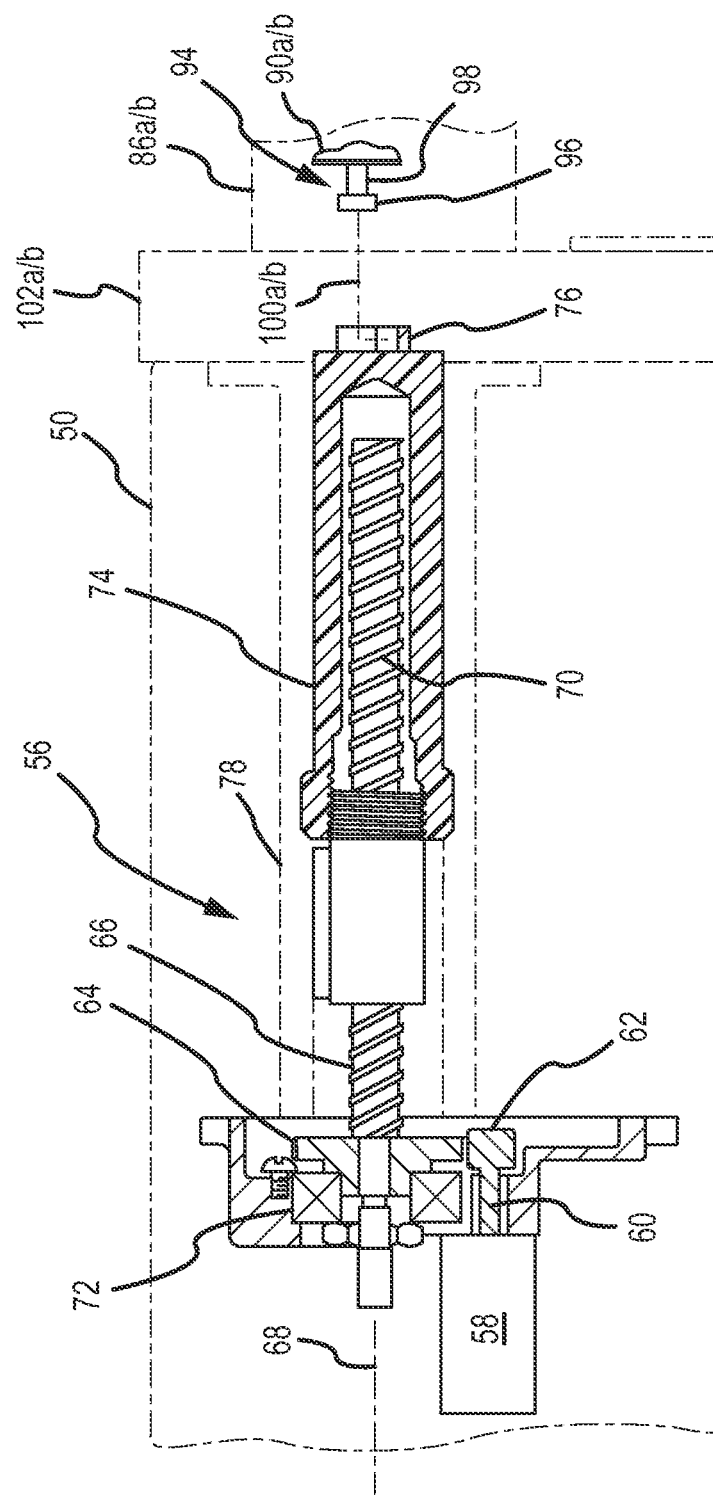
FIG. 2C is a schematic of one embodiment of a syringe plunger drive assembly used by the power injector of FIG. 2A.

The powerhead 50 is utilized to discharge fluid from the syringes 86a, 86b in the case of the power injector 40. That is, the powerhead 50 provides the motive force to discharge fluid from each of the syringes 86a, 86b. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86a, 86b. A separate syringe plunger drive assembly 56 may be incorporated into the powerhead 50 for each of the syringes 86a, 86b. In this regard and referring back to FIGS. 2A-B, the powerhead 50 may include hand-operated knobs 80a and 80b for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86a/b. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90a/b of the corresponding syringe 86a/b. When the ram coupler 76 and syringe plunger coupler 94 are appropriately coupled, the syringe plunger 90a/b moves along with ram 74. FIG. 2C illustrates a configuration where the syringe 86a/b may be moved along its corresponding axis 100a/b without being coupled to the ram 74. When the syringe 86a/b is moved along its corresponding axis 100a/b such that the head 96 of its syringe plunger 90a/b is aligned with the ram coupler 76, but with the axes 68 still in the offset configuration of FIG. 2C, the syringe 86a/b may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation CT imaging, MRI, SPECT imaging, PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

Figure 3A:
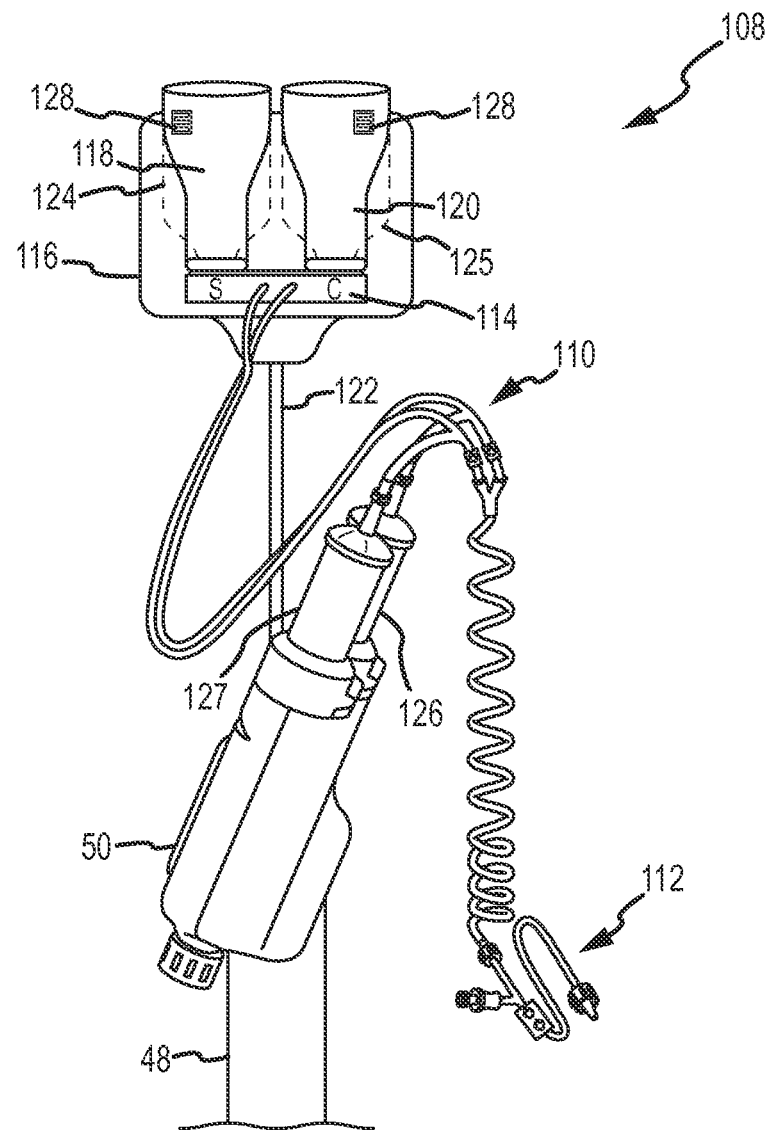
FIG. 3A is a perspective view of one embodiment of a multi-dose injection system.

FIG. 3A is a perspective view of one embodiment of a multi-dose injection system 108. The multi-dose injection system 108 may include the power injector 40 (the powerhead 50 of the power injector 40 is illustrated in FIG. 3A; other portions of the power injector 40 are not illustrated in FIG. 3A). The multi-dose injection system 108 may include a multi-use tubing or tube set 110 (described with reference to FIG. 4A) and a patient-specific tubing or tube set 112 (described with reference to FIG. 4B, and which may also be characterized as a "per-patient disposable 112"). Furthermore, the multi-dose injection system 108 may include a cassette 114 (described with reference to FIGS. 5A and 5B) and a bulk fluid container holder module 116. In the multi-dose injection system 108, fluid may be transferred from the bulk fluid container holder module 116, through the multi-use tubing set 110, through the patient-specific tubing set 112, and into a patient (e.g., into the vasculature of the patient through a catheter or the like). The multi-dose injection system 108 may be operable to transfer and/or mix fluids from one or more bulk containers and be utilized to deliver the same to one or more patients. In this regard, the multi-dose injection system 108 may allow for safe and easy use of bulk containers as well as multiple uses (e.g., across multiple patients) of a saline syringe 126, a contrast syringe 127 and the multi-use tubing set 110.

For use in the multi-dose injection system 108, the syringes 126, 127 may be provided empty. Furthermore, each syringe 126, 127 may be of any appropriate configuration. As shown in FIG. 3A, the saline syringe 126 (the syringe fluidly connected to the saline bottle 118) may be of the same configuration as the contrast syringe 127 (the syringe fluidly connected to the contrast bottle 120). Accordingly, generic empty syringes may be supplied that are operable to be installed in either of the syringe mounting locations on the powerhead 50 and used as either a saline syringe 126 or a contrast syringe 127.

The bulk fluid container holder module 116 may be operable to hold a saline bottle 118 and a contrast bottle 120 for delivery of saline and/or contrast to a single patient and/or to a plurality of patients. Such a configuration may be used, for example, in delivering contrast and saline in connection with an imaging procedure such as MRI and CT imaging. In other embodiments, the bulk fluid container holder module 116 may be configured to hold any appropriate type and number of bulk containers. The number and/or type of bulk containers may correspond to a particular medical fluid delivery procedure. Any appropriate fluid may be contained in each individual bulk container installed on the bulk fluid container holder module 116.

The bulk fluid container holder module 116 may be supported by a support 122. The support 122 may be adjustable such that the height of the bulk fluid container holder module 116 may be adjusted. The support 122 may generally be adjusted such that the bulk fluid container holder module 116 is disposed at a level higher than the powerhead 50. Such positioning allows flow from the bulk fluid container holder module 116 to the powerhead 50 to be assisted by gravity. The support 122 may, for example, be in the form of a vertical pole. The support 122 may be a stand-alone unit or it may be attachable to, and supportable by, another component of the multi-dose injection system 108, such as the portable stand 48 for the powerhead 50.

The bulk fluid container holder module 116 may include two container holders: a saline container holder 124 and a contrast container holder 125. As shown in FIG. 3A, the container holders 124, 125 may correspond to the shapes of the saline bottle 118 and the contrast bottle 120, respectively. For example, as shown in FIG. 3A, the container holders 124, 125 may comprise recesses to accommodate the bottle 118, 120, respectively, and the recesses may be shaped to correspond to the shapes of the bottles 118, 120. The container holders 124, 125 may cradle (e.g., support the bottles 118, 120 by contacting them with portions of the container holders 124, 125 that correspond to the shape of portions of the bottles 118, 120) the containers (e.g., saline bottle 118, contrast bottle 120) disposed therein. The saline bottle 118 and the contrast bottle 120 may, for example, each be 500 milliliter bottles or of any other appropriate size. The saline bottle 118 and the contrast bottle 120 may be held such that the openings of the bottles 118, 120 are facing downward. The openings may be fluidly connected to the cassette 114.

In other embodiments, the container holders 124, 125 may be shaped to correspond to different shaped bottles, fluid bags, or any other appropriate type of bulk fluid container. Such containers may be of any appropriate volume and/or shape. Each container holder 124, 125 may be configured to hold a bulk container in a predetermined position such that a fluid outlet of the bulk container is downwardly disposed. Moreover, in systems that include multiple container holders, each container holder may be specifically configured for a particular bulk container (e.g., one or more of the container holders may be configured differently from one or more other container holders in a particular multi-dose injection system 108). For example, the saline bottle 118 may be shaped such that it is inoperable to be installed into the contrast container holder 125. Furthermore, the container holders 124, 125 may be adjustable to accommodate different types of bulk containers.

The bulk fluid container holder module 116 may include componentry operable to warm one or more bulk containers disposed therein. Any appropriate means for heating the bulk containers may be utilized. For example, the bulk fluid container holder module 116 may include one or more resistive elements disposed along one or more surfaces of the container holders 124, 125 such that heat generated by the one or more resistive elements may be transferred to the bulk containers, thus heating the fluid therein. In this regard, the container holders 124, 125 may cradle (e.g., surfaces of the container holders 124, 125 may correspond to portions of the shape of the bottles 118, 120) bottles 118, 120 inserted therein, resulting in a contact area that may aid the transfer of heat from the container holders 124, 125 to the bottles 118, 120. The bulk fluid container holder module 116 may include sensors operable to sense the temperature of various members such as, for example, fluid contained within the bulk containers and/or surfaces of the container holders 124, 125. The temperature to which the bulk containers may be heated may be adjustable. The bulk fluid container holder module 116 may, for example, be operable to warm any one or more of the bulk containers disposed therein to level at or near body temperature.

The bulk fluid container holder module 116 may be configured such that the cassette 114 may be removably and replaceably fixed to the bulk fluid container holder module 116. For example, the bulk fluid container holder module 116 may contain features that allow the cassette 114 to be snapped into the bulk fluid container holder module 116. It may be such that the cassette 114 can be both detachably installed on and removed from the bulk fluid container holder module 116 by hand—without the use of any tools. Other types of mechanisms, such as screws, spring-loaded pins, magnets, or any other appropriate mechanism may be used to removably and replaceably fix the cassette 114 to the bulk fluid container holder module 116.

The bulk fluid container holder module 116 may include one or more radio frequency identification (RFID) tag readers capable of reading RFID tags. The one or more RFID tag readers may be operable to read a bottle RFID tag 128 disposed on each container (e.g., both the saline bottle 118 and the contrast bottle 120) installed in the bulk fluid container holder module 116. The information read from the bottle RFID tag 128 may be used in a plurality of different ways including, for example, verification of correct bulk container, notification of a change of a bulk container, and tracking of the length of time a bulk container has been connected to the bulk fluid container holder module 116. The information read from the bottle RFID tag 128 may include, for example, lot number, expiration date and/or time, contents, concentration, and/or fill volume. The information read from the bottle RFID tag 128 may be forwarded to the power injector 40 and/or other devices interconnected to the multi-dose injector injection 108. The one or more RFID tag readers may be operable to distinguish which bottle 118, 120 is in which container holder 124, 126. In this regard, the one or more RFID tag readers may be operable to detect a misplaced bottle (e.g., the saline bottle 118 placed in the contrast container holder 125).

The one or more RFID tag readers may be operable to read an RFID tag disposed on the cassette 114. In this regard, the multi-dose injection system 108 may be operable to determine when the cassette 114 has been removed and/or when a new cassette 114 has been installed. The multi-dose injection system 108 may also be operable to determine when a change of cassette 114 is needed and may indicate such a situation (e.g., via the GUI 52 and/or via an audible alert) to an operator (e.g., medical personnel) of the multi-dose injection system 108.

Other appropriate methods of bottle 118, 120 and/or cassette 114 identification and information handling, either singularly or in cooperation, may be employed by the multi-dose injection system 108. For example, machine-readable labels (e.g., barcodes) and/or human-readable labels may be employed to perform some of the functions of the RFID tags and readers discussed above.

The bulk fluid container holder module 116 may include color-coding and/or other visual indicators to aid the operator in setting up the multi-dose injection system 108. For example, the saline bottle 118 may include a purple portion (e.g., on the label, attached to the bottle) that coincides with a purple portion disposed within the saline container holder 124 where the saline bottle 118 is to be installed. In this regard, the operator may match the saline bottle 118 (that includes the purple portion) to the saline container holder 124 (that includes the purple portion). Similarly, the contrast bottle 120 and corresponding contrast container holder 125 may be color-coded with, for example, yellow features. Of course, any appropriate colors and/or symbols may be used as visual indicators to aid the operator in setting up the multi-dose injection system 108.

Figure 5A:
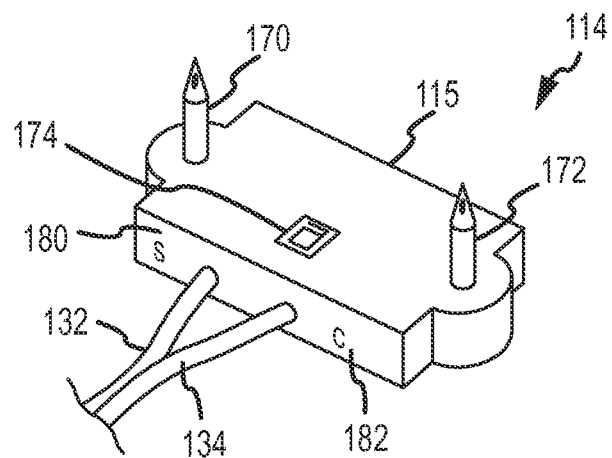
FIG. 5A is a perspective top view of a cassette used by the multi-dose injection system of FIG. 3A.
Figure 5B:
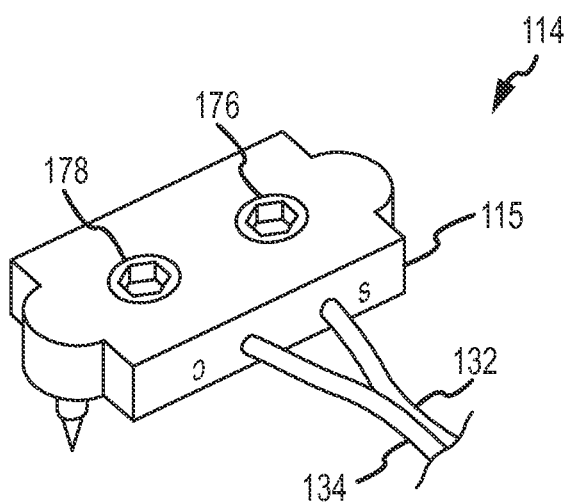
FIG. 5B is a perspective bottom view of the cassette of FIG. 5A.

Turning briefly to FIG. 5B, the cassette 114 may include a saline valve 176 and a contrast valve 178. The bulk fluid container holder module 116 may include valve actuators 130, 131 (FIG. 3B) operable to actuate the valves 176, 178 of the cassette 114. Each valve 176, 178 may be actuatable by rotating a female hexagonal member associated with the particular valve 176, 178. The valves 176, 178 may be of any appropriate configuration (e.g., stop-cock type valves) and operable to control the flow of fluid therethrough. In this regard, the valves 176, 178 may be operable to be continuously adjustable from a fully closed position to a fully opened position.

The bulk fluid container holder module 116 and/or the cassette 114 may include features that enable the multi-dose injector system 108 to determine the positions of the valves 176, 178 after the cassette 114 has been installed onto the bulk fluid container holder module 116. For example, the valves 176, 178 may feature hard stops that prevent the female hexagonal members from freely rotating through 360 degrees. Accordingly, the valve actuators 130, 131 may drive the valves 176, 178 until the valves 176, 178 bump up against the hard stops, at which time the positions of the valves 176, 178 would be known. In another example, the cassette 114 may include switches (and associated electrical connections) that may be actuated when the valves 176, 178 are in a particular position (e.g., open or closed) and the multi-dose injector system 108 may be able to read the actuated switches to determine the position of the valves 176, 178. In still another example, the valves 176, 178 may include indicators (e.g., visual, magnetic) as to their position and the bulk fluid container holder module 116 may include sensors operable to determine the position of the valves 176, 178 based on sensing the indicators.

Figure 3B:
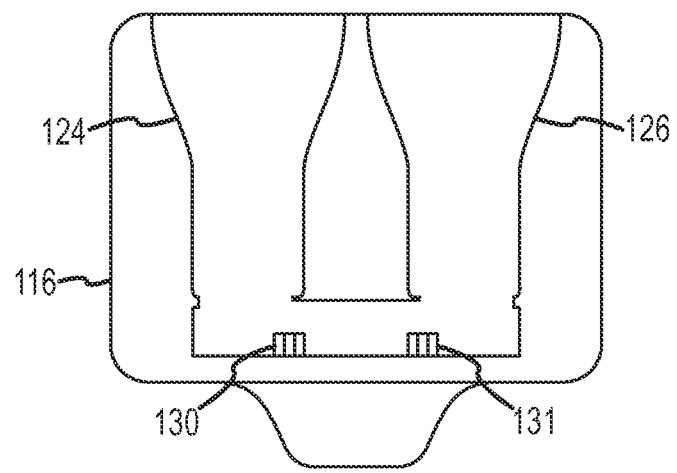
FIG. 3B is a perspective view of a bulk fluid container holder module that may be used by the multi-dose injection system of FIG. 3A.

FIG. 3B is a perspective view of the bulk fluid container holder module 116 with the cassette 114, saline bottle 118 and contrast bottle 120 removed. The saline valve actuator 130 and the contrast valve actuator 131 of the bulk fluid container holder module 116 may comprise hexagonal male protrusions operable to interface with the corresponding female hexagonal members of the corresponding valves 176, 178. The valve actuators 130, 131 may each include a motor or any other appropriate mechanism to rotate the hexagonal male protrusions to adjust the valves 176, 178. Although shown in FIGS. 5B and 3B as hexagonally keyed, any appropriate method of mechanically interfacing the valve actuators 130, 131 of the bulk fluid container holder module 116 with the valves 176, 178 of the cassette 114 may be incorporated into the multi-dose injection system 108. Furthermore, any other appropriate method of actuation of the valves 176, 178 of the cassette 114 may be utilized.

Returning to FIG. 3A, the bulk fluid container holder module 116 may include one or more sensors operable to detect a fluid level within the saline bottle 118 and/or contrast bottle 120. For example, optical sensors may be disposed close to the opening of the saline bottle 118 and/or contrast bottle 120 to detect when a the saline bottle 118 and/or contrast bottle 120 is empty or close to empty. Any appropriate type of sensor or sensors disposed in any appropriate location or locations may be utilized by the bulk fluid container holder module 116. The sensors may be disposed to generally detect fluid volume levels within the attached saline bottle 118 and/or contrast bottle 120, or the sensors may be disposed to detect when the volume within saline bottle 118 and/or contrast bottle 120 reaches a certain level (e.g., close to empty).

The bulk fluid container holder module 116 may be operable to communicate with other portions of the multi-dose injection system 108. In this regard, the various features of the bulk fluid container holder module 116 discussed herein may be controlled by and/or directed by components located in other portions of the multi-dose injection system 108 (e.g., the powerhead 50 and/or GUI 52 of the powerhead 40). For example, actuation of the valve actuators 130, 131 may be controlled by, and synchronized with, the powerhead 50. The bottle heaters of the bulk fluid container holder module 116 may be controlled by the powerhead 50 (e.g., a user may turn on and off the bottle warmer(s) and set the set temperature of the bottle warmer(s) from the GUI 52). Moreover, the bulk fluid container holder module 116 may communicate RFID tag information obtained from the bottles 118, 120 and/or cassette 114 installed into the bulk fluid container holder module 116 to the powerhead 50 or other appropriate component of the multi-dose injection system 108. The bulk fluid container holder module 116 may communicate fluid level information (e.g., obtained from the sensors discussed above). The communications between the bulk fluid container holder module 116 and other components of the multi-dose injection system 108 may be via any appropriate method or technology, including a direct electrical connection (e.g., wired) or a wireless connection.

The illustrated bulk fluid container holder module 116 and accompanying discussion related to the bulk fluid container holder module 116 describe container holders 124, 125 designated for the saline bottle 118 and a contrast bottle 120. However, the bulk fluid container holder module 116 may be configured to hold any appropriate number of containers for a particular application or procedure. For example, an embodiment of a multi-dose injection system 108 may include a single container holder for procedures where only a single fluid source is needed. For a further example, an embodiment of a multi-dose injection system 108 may include three or more container holders for procedures where three or more different fluid sources may be required. In still a further example, an embodiment of a multi-dose injection system 108 may include three or more container holders where some of the container holders hold separate bulk containers containing the same type of fluid. Such a system may be used to aid in bulk container replacement and/or to be operable to continue to deliver fluids when one of the bulk containers becomes empty or close to empty.

The bulk fluid container holder module 116 in conjunction with the powerhead 50 may be operable to transfer fluids from either bottle 118, bottle 120, or from both bottle 118 and bottle 120. Such transfers may be done sequentially or simultaneously. For example, a particular patient may only receive contrast during a particular procedure, in which case contrast from the contrast bottle 120 would be loaded into the contrast syringe 127 installed on the powerhead 50. In another example, a patient may first receive a dose of saline, followed by a dose of contrast (or vice versa), in which case contrast from the contrast bottle 120 would be loaded into the contrast syringe 127 installed on the powerhead 50 and saline from the saline bottle 118 would be loaded into the saline syringe 126 installed on the powerhead 50. In another example, a patient may receive a dose of saline and simultaneously receive a dose of contrast, in which case contrast from the contrast bottle 120 could be loaded into the contrast syringe 127 installed on the powerhead 50 and saline from the saline bottle 118 could be loaded into the saline syringe 126 installed on the powerhead 50. The two fluids may mix together in the multi-use tubing set 110, effectively delivering a diluted dose of contrast to the patient.

Figure 4A:
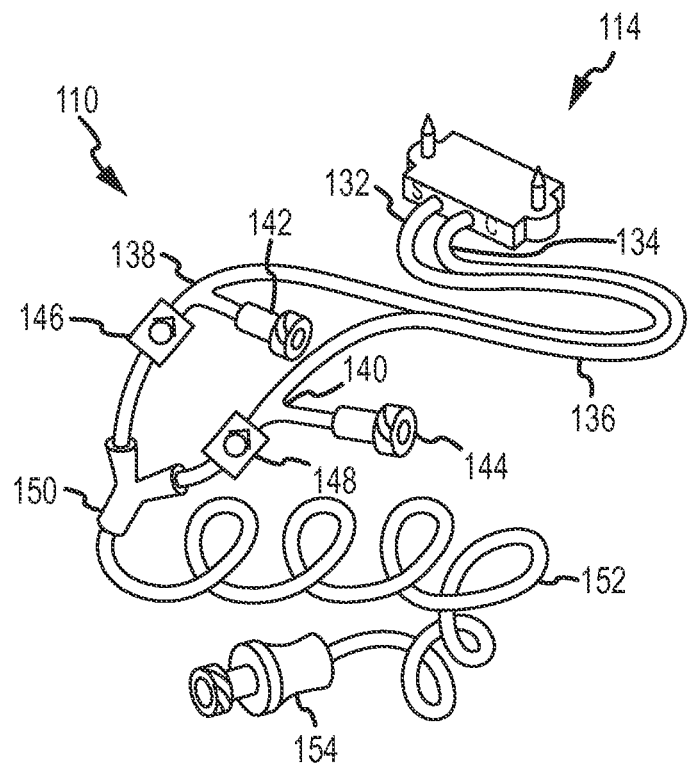
FIG. 4A is a perspective view of a multi-use tubing set that may be used by the multi-dose injection system of FIG. 3A.
Figure 4B:
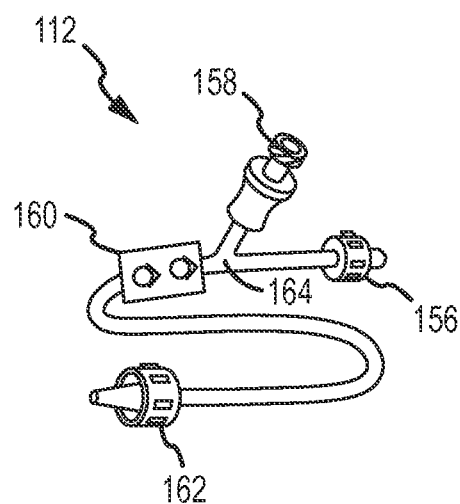
FIG. 4B is a perspective view of a patient-specific tubing set that may be used by the multi-dose injection system of FIG. 3A.

FIG. 4A is a perspective view of the multi-use tubing set 110 and FIG. 4B is a perspective view of the patient-specific tubing set 112. The multi-use tubing set 110, as illustrated in FIG. 4A, may be permanently interconnected to the cassette 114. In this regard, the multi-use tubing set 110 and the cassette 114 may be packaged together and replaced as a single unit. Alternatively, the cassette 114 and the multi-use tubing set 110 may be separate items that may be interconnected to each other (e.g., using Luer connectors, barbs).

Fluidly interconnected to the cassette 114 are two fluid tubes: a saline tube 132 and a contrast tube 134. The tubes 132, 134 may be of any appropriate construction for directing the flow of fluid between various locations. The tubes 132, 134 may fluidly connect the cassette 114 with the corresponding nozzles of the syringes 126, 127 on the powerhead 50. In this regard, the saline tube 132 may be fluidly interconnected to a saline connector 142. The saline connector 142 may be in the form of a Luer type connector operable to directly connect to the nozzle of the saline syringe 126 on the powerhead 50. The contrast tube 134 may be fluidly interconnected to a contrast connector 144. The contrast connector 144 may be in the form of a Luer type connector operable to directly connect to the nozzle of the contrast syringe 127 on the powerhead 50. For the connections between the saline tube 132 and the contrast tube 134 and their corresponding nozzle, any appropriate fluid connector may be substituted for the Luer connectors described herein.

The saline tube 132 may be interconnected to the saline connector 142 via a saline Y connector 138 (or any other appropriate connector), or the saline connector 142 may simply be associated with a short extension tube that leads into the saline tube 132. The saline Y connector 138 may also be fluidly interconnected to a saline and contrast tubes Y connector 150. Positioned between the saline Y connector 138 and the saline and contrast tubes Y connector 150 may be a saline tube one-way check valve 146. The saline tube one-way check valve 146 may be operable to only permit fluid flow in the direction from the saline Y connector 138 to the saline and contrast tubes Y connector 150. The saline tube one-way check valve 146 may require a pressure equal to or greater than a cracking pressure (e.g., the minimum upstream pressure at which the saline tube one-way check valve 146 will operate) to be present upstream of the saline tube one-way check valve 146 before the saline tube one-way check valve 146 will open and allow fluid to flow. Similarly, the contrast tube 134 may be interconnected to the contrast connector 144 via a contrast Y connector 140 (or any other appropriate connector), or the contrast connector 144 may simply be associated with a short extension tube that leads into the contrast tube 134. The contrast Y connector 140 may also be fluidly interconnected to the saline and contrast tubes Y connector 150. Positioned between the contrast Y connector 140 and the saline and contrast tubes Y connector 150 may be a contrast tube one-way check valve 148. The contrast tube one-way check valve 148 may be configured similarly to the saline tube one-way check valve 146 and may be operable to only permit fluid flow in the direction from the contrast Y connector 140 to the saline and contrast tubes Y connector 150. Together the saline tube one-way check valve 146 and contrast tube one-way check valve 148 permit fluid to flow from the saline syringe 126 and contrast syringe 127 of the powerhead 50 to the patient, while at least attempting to prevent backflow in the opposite direction.

As illustrated in FIG. 4A, the saline tube 132 and the contrast tube 134 may be joined together (although not fluidly joined together) in a joined tube section 136. Such an arrangement helps to reduce tangling of tubes such as may occur if the saline tube 132 and the contrast tube 134 were completely separate from each other. The saline tube 132 and the contrast tube 134 may be of any appropriate length. For example, the tubes 132, 134 may be of a length such that the cassette 114, attached to the bulk fluid container holder module 116, may be positioned above the powerhead 50 such that gravity may aid in the flow of saline and contrast from the bulk fluid container holder module 116 down to the powerhead 50.

The saline tube 132 may be configured with an internal diameter appropriate for the viscosity of saline and the flow rate and pressure expected therein during medical fluid delivery procedures. Furthermore, the saline tube 132 wall thickness and material of the saline tube 132 may be selected, inter alia, based on expected pressures during fluid delivery procedures. Similarly, the contrast tube 134 may be configured with an internal diameter appropriate for the viscosity of the contrast to be used and the flow rate and pressure expected therein during medical fluid delivery procedures. The contrast tube 134 wall thickness and material of the contrast tubes 134 may be selected, inter alia, based on expected pressures during fluid delivery procedures.

The saline connector 142 and the contrast connector 144 may be color-coded or otherwise marked to aid in the setting up of the multi-dose injection system 108. For example, continuing the color scheme discussed above with respect to the marking of the saline bottle 118, the saline connector 142 may be color-coded purple. Furthermore the nozzle and/or other portion of the saline syringe 126 on the powerhead 50 may also be color-coded purple. Along these same lines, the contrast connector 144 and the corresponding nozzle and/or other portion of the contrast syringe 127 on the powerhead 50 may be color-coded yellow. Furthermore, the saline connector 142 and the contrast connector 144 may be uniquely configured (e.g., uniquely keyed, uniquely sized) such that each of the connectors 142, 144 is only operable to be attached to its corresponding nozzle from the corresponding syringe 126, 127.

Interconnected to the saline and contrast tubes Y connector 150 may be an extension tube 152. The extension tube 152 may be coiled to aid in the handling of the extension tube 152 and to reduce tangling. The extension tube 152 may be of any appropriate length. For example, the extension tube 152 may be of a length to accommodate the typical distance between the powerhead 50 and the patient-specific tubing set 112 that may be seen before, during, and after an imaging procedure utilizing the multi-dose injection system 108.

At the end of the extension tube 152 opposite from the saline and contrast tubes Y connector 150 may be a needle-free swabable female Luer connector 154. Catheters inserted into a patient typically have a female Luer connector. By having a female Luer connector 154 at the end of the extension tube 152, accidental attachment of the female Luer 154 directly to a catheter installed in a patient should be prevented (e.g., due to the inability of the female Luer connector connected to the catheter to directly connect to the female Luer connector 154 at the end of the extension tube 152). Thus, the chances of contaminating the multi-use tubing set 110 with patient fluids should be reduced. In this regard, a unique tubing set with male Luer connectors on each end, such as the patient-specific tubing set 112 described below, is required to interconnect the extension tube 152 to a catheter in a patient. Furthermore, the female Luer connector 154 is swabable and therefore may be cleaned before being fluidly interconnected to a new patient-specific tubing set 112.

As noted, and now referring to FIG. 4B, the patient-specific tubing set 112 may include two male luer connections: a male Luer 156 operable to interconnect to the female Luer 154 (from the multi-use tubing set 110) and a patient interface male Luer 162 operable to interconnect to, for example, a catheter inserted into the patient. The patient-specific tubing set 112 may include an alternate access port such as access Luer 158. The access Luer 158 may be used, for example, to check the patency of a catheter inserted into the patient and connected via the patient interface male Luer 162. The access Luer 158 may be used to, for example, deliver alternate fluids (e.g., alternate to the saline or contrast) to the patient. The access Luer 158 may be used for any other appropriate procedure and/or fluid delivery. Any other appropriate type of fluid access device may be added to or substituted for the access Luer 158.

The patient-specific tubing set 112 may also include dual one-way check valves 160. The dual one-way check valves 160 may prevent fluid flow in a direction from the patient interface male Luer 162 toward the male Luer 156. In this regard, the dual one-way check valves 160 may reduce the potential for contamination of the multi-use tubing set 110 with fluids from the patient. This then should enable the use of the multi-use tubing set 110 to supply fluid to several patients by reducing the potential of fluid from a particular patient mixing with fluids from another patient. The dual one-way check valves 160 may comprise two serially-disposed individual one-way check valves. Such an arrangement provides a level of redundancy in that if one of the one-way check valves fails, the other one-way check valve may remain functional and reduce the potential of backflow of fluids from the patient into the multi-use tubing set 110.

The dual one-way check valves 160 of the patient-specific tubing set 112 are positioned downstream (e.g., relative to the normal flow of fluids through the patient-specific tubing set 112) of a Y connector 164. In alternate configurations, the dual one-way check valves 160 may be disposed upstream of the Y connector 164 between the Y connector 164 and the male Luer 156. In another arrangement, one one-way valve of the dual one-way check valves 160 may be disposed on each side of the Y connector 164. Any other appropriate configuration of the one-way check valves of the dual one-way check valves 160 may be utilized in the patient-specific tubing set 112.

FIG. 5A is a perspective top view of the cassette 114 used by the multi-dose injection system 108. FIG. 5B is a perspective bottom view of the cassette 114 of FIG. 5A. The cassette 114 may be selectively securable to the bulk fluid container holder module 116. The cassette 114 may include features that correspond to features on the bulk fluid container holder module 116 so that the cassette 114 may be secured to the bulk fluid container holder module 116. For example, the cassette 114 may snap into the bulk fluid container holder module 116. Clips, screws or the like may be used to secure the cassette 114. Any other appropriate means of selectively securing the cassette 114 to the bulk fluid container holder module 116 may be employed.

The cassette 114 may include an identification feature such as a cassette RFID tag 174. The bulk fluid container holder module 116 may include an RFID tag reader (not shown) operable to read the RFID tag 174 attached to the cassette 114. In this regard, the bulk fluid container holder module 116 may be operable to determine information regarding the cassette 114. Such information may include, for example, cassette 114 part number, cassette 114 serial number, and cassette 114 configuration information. Such information may be communicated to other components of the multi-dose injection system 108. Such information may, for example, be used for operational, validation, or recordation purposes. Furthermore, using the cassette RFD tag 174 to track the presence of the cassette 114 attached to the bulk fluid container holder module 116 and tracking the flow of fluid from the bulk fluid containers interconnected to the cassette 114, a usage history of the cassette 114 may be developed. Such a usage history may be used to determine, for example, when to replace the cassette 114 (and optionally also the multi-use tubing set 110 connected to the cassette 114) and/or when to replace the saline bottle 118 and/or contrast bottle 120. Moreover, the RFID tag reader may be operable to detect when a particular cassette 114 is removed and/or replaced with a different cassette 114.

The cassette RFID tag 174 may be disposed in any appropriate location on the cassette 114. The RFID tag reader may be disposed in any appropriate location on the bulk fluid container holder module 116 or on any other appropriate component of the multi-dose injection system 108.

As illustrated, the cassette 114 includes two bulk fluid container fluid interfaces in the form of a saline spike 170 and a contrast spike 172. The spikes 170, 172 may be vented to allow air to flow into the bottles 118, 120 as fluid flows out of the bottles 118, 120. Where appropriate, for example where the bulk fluid containers are collapsible, the spikes 170, 172 may not include vents. The cassette 114 may include an appropriate number of bulk fluid container fluid interfaces. The spikes 170, 172 may be fixedly secured to the cassette 114 and disposed such that they are pointing upward from the cassette 114 when the cassette 114 is secured to the bulk fluid container holder module 116. In this regard, fluid containers such as the saline bottle 118 (FIG. 3A) may be fluidly interconnected to the cassette 114 by pressing and/or lowering the saline bottle 118 onto the saline spike 170. The fluid interconnection may be achieved by the saline spike 170 piercing a septum or other pierceable barrier of the saline bottle 118 as the saline bottle 118 is lowered onto the saline spike 170. The saline bottle 118 may be removed from the cassette 114 by pulling upward on the saline bottle 118. Additionally, when fluidly connected to the saline spike 170, additional securement features, such as clips, twist locks, snaps, or any other appropriate securement device or devices, may be used to further secure the saline bottle 118 onto the saline spike 170. The contrast bottle 120 may be secured to the contrast spike 172 in a similar manner.

The saline spike 170 may be fluidly interconnected to the saline valve 176 that is in turn fluidly connected to the saline tube 132. The saline valve 176 may be a stop-cock type valve operable to vary between a fully open (e.g., no restriction to fluid flow between the saline spike 170 and the saline tube 132) and a fully closed (e.g., no flow between the saline spike 170 and the saline tube 132) position. The saline valve 176 may also be operable to be positioned in intermediate positions allowing partial fluid flow therethrough. The saline valve 176 may be disposed within a housing 115 of the cassette 114. The housing 115 may also contain a portion of the saline spike 170 and fluid passages fluidly connecting the saline tube 132 to the saline valve 176 and the saline spike 170 to the saline valve 176. The contrast spike 172 and the contrast tube 134 may be fluidly connected to a similarly configured contrast valve 178. The contrast valve 178 may be configured similarly to the saline valve 176.

The cassette 114 may include saline indicia 180 to assist the user in determining the proper location for installation of the saline bottle 118. The saline indicia 180 may be in the form of a symbol, such as the letter S. Furthermore, the saline indicia 180 may be color-coded purple (or any other appropriate color). The cassette 114 may include contrast indicia 182, such as the letter C. The contrast indicia 182 may be color-coded yellow (or any other appropriate color).

Valve 176, 178 operation will be now be described in the exemplary configuration where the contrast valve 178 is fluidly interconnected to the contrast syringe 127 on the powerhead 50. It will be appreciated that the flow of saline may be controlled in a similar manner and that a particular fluid source (e.g., saline bottle 118, contrast bottle 120) may be fluidly interconnected to any appropriate syringe 126, 127 on the powerhead 50. The contrast valve 178 may be used in conjunction with the movement of the contrast syringe 127 on the powerhead 50 to achieve the transfer of contrast from the contrast bottle 120 through the cassette 114, the multi-use tubing set 110, the patient-specific tubing set 112 and into the patient. To achieve such a flow, the contrast valve 178 may be disposed in an open position during the retraction of a plunger of the contrast syringe 127. During such retraction, a vacuum force may be generated in the contrast syringe 127 and communicated to the attached contrast tube 134, thereby loading fluid from the contrast bottle 120 into the contrast syringe 127. The contrast tube one-way check valve 148 may prevent fluid from portions of the multi-use tubing set 110 downstream of the contrast tube one-way check valve 148 from flowing into the contrast syringe 127. Once a satisfactory amount of fluid has been loaded into the contrast syringe 127, the contrast valve 178 may be closed and the plunger of the contrast syringe 127 may be advanced. The closed contrast valve 178 may prevent contrast from flowing back into the contrast bottle 120. Meanwhile, the contrast tube one-way check valve 148 may permit flow therethrough from the contrast syringe 127 into the extension tube 152, the patient-specific tubing set 112 and into the patient. Similar manipulation of the saline valve 176 and the corresponding saline syringe 126 of the powerhead 50 may be operable to facilitate transfer of saline from the saline bottle 118 into the patient.

The valves 176, 178 may include features to facilitate their actuation by the bulk fluid container holder module 116. As illustrated in FIG. 5B, valves 176, 178 may each include a female hex. Such female hexes may be operable to interface with corresponding male hex protrusions (not shown) of the bulk fluid container holder module 116. The male hex protrusions may engage with the female hexes on the cassette 114 as the cassette 114 is inserted into the bulk fluid container holder module 116. Accordingly, the bulk fluid container holder module 116 may include members (e.g., motors) operable to drive (e.g., rotate) the male hex protrusions in order to actuate (e.g., open, close) the valves 176, 178. Such actuation of the valves 176, 178 may be controlled by a control member (e.g., hardware and/or software) disposed in any appropriate component or combination of components of the multi-dose injection system 108. For example, the control member may be disposed within the powerhead 50. Thus synchronization between movement of the plungers of the syringes 126, 127 on the powerhead 50 and the positions of the valves 176, 178 may be achieved. Any other appropriate means of actuating the valves 176, 178 may be utilized by the multi-dose injection system 108. For example: protrusions shaped differently than hexes may be used; the locations of the male and female protrusions may be reversed; other types of interfaces such as a magnetic interface may be used; or the cassette 114 may include valve position driving members (e.g., motors) and may be controlled through an electronic interface (e.g., electrical contacts) between the bulk fluid container holder module 116 and the valves 176, 178.

Figure 6:
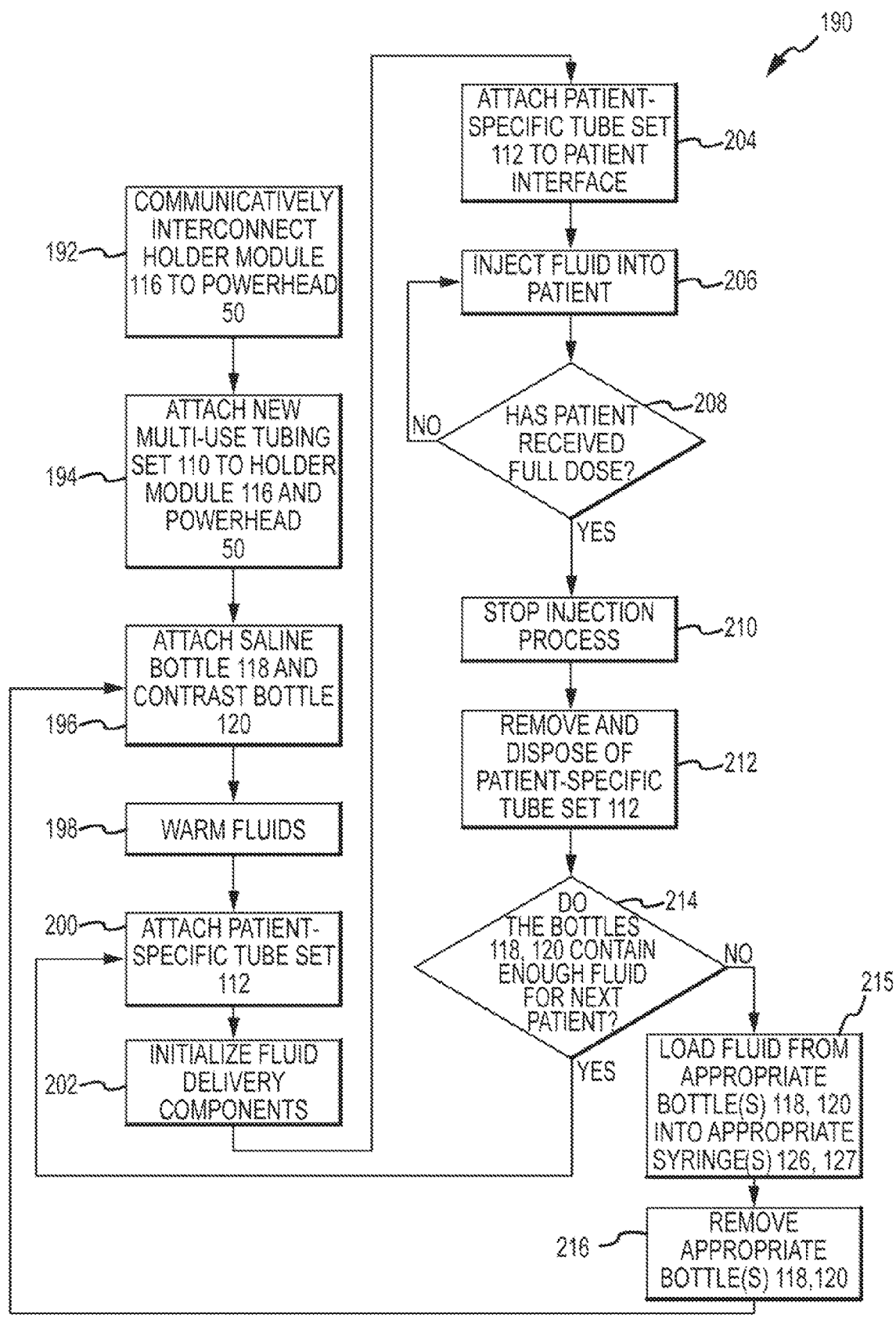
FIG. 6 is a flowchart of a method of delivering medical fluid to a plurality of patients from the multi-dose injection system.

FIG. 6 is a flowchart of a method 190 of delivering medical fluid to a plurality of patients from the multi-dose injection system 108. The first step 192 in the method 190 may be to communicatively interconnect the bulk fluid container holder module 116 to an injection device (e.g., powerhead 50) via a communications link. The communications link may be a hardwired electrical cable, a wireless connection, or any other appropriate communications link. The remainder of the present method 190 is described in the context of delivering saline using the saline syringe 126 on the powerhead 50 and contrast using the contrast syringe 127 on the powerhead 50. It will be appreciated that the syringes 126, 127 may be reversed or that, in other embodiments, other types of fluids may be delivered.

The following step 194, may be to attach a new multi-use tubing set 110 to the bulk fluid container holder module 116 and the powerhead 50. The multi-use tubing set 110 may be pre-connected to the cassette 114. This attachment may include inserting the cassette 114 into a corresponding receiving location in the bulk fluid container holder module 116. The next portion of the current step 194 may be to interconnect the saline connector 142 to the corresponding nozzle on the saline syringe 126 of the powerhead 50. This may be followed by interconnecting the contrast connector 144 to the nozzle of the contrast syringe 127. The current step 194 may also include reading the cassette RFID tag 174 with an RFID tag reader. The multi-dose injection system 108 may verify that the correct cassette 114 has been installed for the procedure to be performed by the multi-dose injection system 108. Furthermore, the current step 194 may include determining the position of the valves 176, 178 by the multi-dose injector system 108 using the components of the bulk fluid container holder module 116 and/or the cassette 114 discussed above. The current step 194 may also include actuating the valves 176, 178 such that they are in a predetermined configuration (e.g., closed to prevent flow between the bottles 118, 120 and the multi-use tubing set 110).

This may be followed by the step 196 of fluidly attaching the saline bottle 118 and the contrast bottle 120 to the cassette 114. The user may be aided in this step 196 by color-coding on the bottles 118, 120, container holders 124, 125, and/or the cassette 114. For example, the saline bottle 118, the saline container holder 124, and the saline indicia 180 on the cassette 114 may all be color-coded purple to assist the user. Similarly, contrast related components may be color-coded yellow. Any other appropriate color-coding scheme may be used. The attaching of the bottles 118, 120 may comprise lowering the bottles 118, 120 onto corresponding spikes 170, 172 of the cassette 114.

The next step 198 may be to warm the fluids in the bottles 118, 120. This may be accomplished by energizing resistive heating elements disposed in the container holders 124, 125. The fluids in the bottles 118, 120 may be heated to a preset temperature (e.g., the internal temperature of the patient who is to receive the fluids). Alternatively, any appropriate method of heating fluid within the bottles 118, 120 may be used. The bottles 118, 120 may be heated to any appropriate target temperature. The bottles 118, 120 may each be heated to the same temperature, or each bottle 118, 120 may be heated to a different target temperature.

The next step, step 200, may include attaching the patient-specific tubing set 112 to the multi-use tubing set 110. This may include swabbing (e.g., with an alcohol swab) the swabable female Luer connector 154 of the multi-use tubing set 110 to clean and/or sterilize the female Luer connector 154. This may be followed by interconnecting the swabable female Luer connector 154 to the male Luer 156.

The next step 202 may be to initialize fluid delivery components (e.g., the syringes 126, 127, the tubing of the multi-use tubing set 110, and the patient-specific tubing set 112). This step 202 may include orienting the powerhead 50 such that it is pointing upward (e.g., so the nozzles of the syringes 126, 127 are pointing upward). Next the valves 176, 178 may be opened and the plungers of the syringes 126, 127 retracted to load fluid from the bottles 118, 120 into the multi-use tubing set 110 and into the syringes 126, 127. The air within the syringes 126, 127 may accumulate at the top of the syringes 126, 127. Next, the valves 176, 178 may be closed and the plungers of the syringes 126, 127 extended to force the air and fluid within the syringes 126, 127 past the one-way check valves 146, 148, through the extension tube 152, and through the patient-specific tubing set 112. This process may be repeated until at least substantially all air has been expelled from the tubing through the patient interface male Luer 162. The saline tube 132 and the contrast tube 134 may be individually or simultaneously purged using such a process. Moreover, the multi-use tubing set 110 could be purged prior to attaching the patient-specific tubing set 112 (which would thereafter have to be purged). The multi-use tubing set 110 should not have to be re-purged until the bottles 118, 120 are replaced, or until the multi-use tubing set 110 is replaced, although the patient-specific tubing set 112 should be purged each time it is replaced.

The next step 204 may be to connect the patient interface male Luer 162 of the patient-specific tubing set 112 to a corresponding female Luer interconnected to a catheter that has been inserted into the patient. The patency of the catheter may then be verified through the access Luer 158.

The next step 206 may be to inject fluid from the multi-dose injection system 108 to the patient through the catheter. This may include placing the powerhead 50 in a downward-pointing position. In this regard, any air within the syringes 126, 127 or any air that enters the syringes 126, 127 may be trapped within the syringes 126, 127.

The remainder of step 206 and the method 190 will be described in the context of injecting contrast into the patient using the contrast syringe 127 on the powerhead 50. It should be understood that the procedure for injecting saline may be similar. Furthermore, either syringe 126, 127 of the powerhead 50 may be used for the injection of any appropriate fluid.

Continuing with step 206, the contrast valve 178 may be opened and the plunger of the contrast syringe 127 may be retracted to load contrast from the contrast bottle 120 into the contrast syringe 127. During this step, the contrast tube one-way check valve 148 should prevent fluid downstream of the contrast tube one-way check valve 148 from entering the contrast syringe 127. Next, the contrast valve 178 is closed and the plunger of the contrast syringe 127 is extended. The closed contrast valve 178 should prevent fluid from flowing into the contrast bottle 120 and the contrast tube one-way check valve 148 permits flow therethrough as the pressure in the contrast tube 134 elevates due to the movement of the plunger of the contrast syringe 127. In this regard, contrast may flow past the contrast tube one-way check valve 148, into the extension tube 152, through the patient specific tubing set 112, through the catheter, and into the patient.

The sequence of contrast valve 178 opening and closing coupled with retraction and extension of the plunger of the contrast syringe 127 may be repeated until the patient has received a predetermined dose of contrast. Accordingly, the next step 208 may be to inquire/determine if the patient has received the full desired dose of contrast. If the patient has not received the full dose, the step 206 of injecting contrast may continue. If the patient has received the full dose, the next step 210 may be to stop the injection process. It should be appreciated that an injection protocol for a particular patient may utilize any appropriate number of phases, and that each phase may use any appropriate fluid (e.g., an injection protocol may entail alternating injections of contrast and saline; an injection protocol may include at least one injection of contrast and at least one injection of saline, or the like).

Once the injection process has been stopped, the next step 212 may be to disconnect the multi-use tubing set 110 from the patient-specific tubing set 112 by disconnecting the swabable female Luer connector 154 from the male Luer 156.

The next step 214 may be to determine if the saline bottle 118 and contrast bottle 120 contain enough fluid for performance of fluid delivery to a subsequent patient. If it is determined that the saline bottle 118, the contrast bottle 120, or both need to be replaced, the next step 215 may be to load any fluid contained in the bottle 118 and/or 120 to be replaced into the appropriate syringe 126 and/or 127. In this regard, the fluid may be available for injection into the next patient. The next step 216 may be to remove the appropriate bottle and move on to step 196 and fluidly attach a new bottle. The process 190 may then be continued for the subsequent patient using a new patient-specific tubing set 112. If it is determined that the bottles 118, 120 do not need to be replaced, the next step in the process 190 may be to move to step 200 and continue the process on the subsequent patient using a new patient-specific tubing set 112.

Once it is determined that the multi-use tubing set 110 is to be replaced, the process 190 may be halted and the multi-use tubing set 110 replaced. The used multi-use tubing set 110 may then be discarded or refurbished (e.g., cleaned and/or sterilized). The determination that the multi-use tubing set 110 is to be replaced may, for example, be based on a predetermined length of time that the multi-use tubing set 110 has been in service, a predetermined volume of fluids moving therethrough, suspected contamination and/or damage, a number of injection protocols that have been executed using the multi-use tubing set 110, or any other appropriate criteria.

The multi-dose injection system 108 may also be operable to perform certain functions related to the changing of the saline bottle 118 and/or contrast bottle 120. For example, when the contrast bottle 120 is near empty, the powerhead 50 may load any remaining contrast into the contrast syringe 127. The user may then replace the contrast bottle 120. The plunger of the contrast syringe 127 may then be extended with the contrast valve 178 open so that any air in the contrast tube 134 is forced into the new contrast bottle 120. Thus, the purge step 202 may be avoided or the amount of purging required may be reduced. In this regard, the contrast bottle 120 may be expandable, have an air pocket, or have any other appropriate feature (e.g., a vent) to allow fluids to be forced therein from the contrast syringe 127.

Additionally, when not injecting fluids into a patient, one or both of the saline valve 176 and the contrast valve 178 may be left in an open position. This may prevent undesired pressure from being built up in the syringes 126, 127 of the powerhead 50.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A multi-dose injection system comprising:
   an injection device comprising first and second syringes;
   a bulk fluid container holder module comprising first and second container holders;
   first and second bulk fluid containers disposed in said first and second container holders, respectively;
   a cassette detachably interconnected with said bulk fluid container holder module and comprising first and second bulk fluid container fluid interfaces, wherein said first and second bulk fluid container fluid interfaces are associated with said first and second container holders, respectively, and are fluidly connected with said first and second bulk fluid containers, respectively; and
   a tubing set comprising a first tubing set portion extending between said first syringe of said injection device and said first bulk fluid container fluid interfaces of said cassette, and a second tubing set portion extending between said second syringe of said injection device and said second bulk fluid container fluid interface of said cassette, wherein fluid from said first bulk fluid container may be loaded into said first syringe through said first bulk fluid container interface of said cassette and said first tubing set portion, and wherein fluid from said second bulk fluid container may be loaded into said second syringe through said second bulk fluid container interface of said cassette and said second tubing set portion.

2. The multi-dose injection system of claim 1, wherein each of said first and second bulk fluid container fluid interfaces comprises a vented spike.

3. The multi-dose injection system of claim 2, wherein said cassette comprises a housing, wherein each said vented spike extends within an interior of said housing, wherein said first tubing set portion is fluidly interconnected to with said vented spike of said first bulk fluid container fluid interface within said interior of said housing, and wherein said second tubing set portion is fluidly interconnected with said vented spike of said second bulk fluid container fluid interface within said interior of said housing.

4. The multi-dose injection system of claim 1, wherein said first container holders is operable to cradle said first bulk fluid container, and wherein said second container holder is operable to cradle said second bulk fluid container.

5. The multi-dose injection system of claim 1, wherein said bulk fluid container holder module comprises a heating member operable to generate heat and transfer said heat to said second bulk fluid container disposed within said second container holder of said bulk fluid container holder module.

6. The multi-dose injection system of claim 1, wherein said bulk fluid container holder module further comprises a bulk fluid container heater.

7. The multi-dose injection system of claim 1, wherein said cassette further comprises first and second valves associated with said first and second bulk fluid container fluid interfaces, respectively.

8. The multi-dose injection system of claim 7, wherein said first valve is operable to fluidly isolate said first bulk fluid container fluid interface from said first tubing set portion, and wherein said second valve is operable to fluidly isolate said second bulk fluid container fluid interface from said second tubing set portion.

9. The multi-dose injection system of claim 7, wherein said cassette comprises a housing, wherein each of said first and second bulk fluid container fluid interfaces comprises a vented spike, wherein each said vented spike extends within an interior of said housing, wherein each of said first and second valves is disposed within said interior of said housing, wherein said first tubing set portion is fluidly interconnected to said vented spike of said first bulk fluid container fluid interface within said interior of said housing, and wherein said second tubing set portion is fluidly interconnected to said vented spike of said second bulk fluid container fluid interface within said interior of said housing.

10. The multi-dose injection system of claim 7, wherein said bulk fluid container holder module comprises first and second valve actuators for said first and second valves, respectively, of said cassette.

11. The multi-dose injection system of claim 10, wherein each of said first and second valve actuators is operable to open and close in synchronization with movement of a plunger of said injection device.

12. The multi-dose injection system of claim 10, wherein a position of each of said first and second valve actuators is electronically controllable.

13. The multi-dose injection system of claim 1, wherein said bulk fluid container holder module comprises a cassette identification reader capable of reading a cassette identification member of said cassette.

14. The multi-dose injection system of claim 13, wherein said cassette identification reader is an RFID reader, wherein said cassette identification member is an RFID tag.

15. The multi-dose injection system of claim 1, wherein said bulk fluid container holder module comprises a bulk fluid container identification reader capable of reading a bulk fluid container identification member connected to said second bulk fluid container.

16. The multi-dose injection system of claim 15, wherein said bulk fluid container identification reader is an RFID reader, wherein said bulk fluid container identification member is an RFID tag.

17. The multi-dose injection system of claim 1, wherein said first bulk fluid container comprises saline and said second bulk fluid container comprises contrast.

18. The multi-dose injection system of claim 1, wherein said cassette and said tubing set are permanently connected to each other.

19. The multi-dose injection system of claim 1, wherein said cassette comprises an RFID tag.

20. The multi-dose injection system of claim 1, further comprising a patient-specific tubing set fluidly connected to said tubing set.

21. The multi-dose injection system of claim 1, wherein said injection device comprises a powerhead.

22. A multi-dose injection system comprising:
an injection device comprising a first syringe;
a bulk fluid container holder module;
a first bulk fluid container installed on said bulk fluid container holder module;
a cassette comprising a first bulk fluid container fluid interface and a first valve, wherein said cassette is detachably interconnected to said bulk fluid container holder module, and wherein said first bulk fluid container fluid interface is fluidly connected with said first bulk fluid container; and
a tubing comprising a first tubing set portion, wherein said first tubing set portion extends from said first syringe of said injection device to said first bulk fluid container fluid interface of said cassette, wherein said first valve is operable to fluidly isolate said first bulk fluid container fluid interface from said first tubing set portion, and wherein said first valve is operable to fluidly connect said first bulk fluid container fluid interface with said first tubing set portion such that fluid from said first bulk fluid container may be loaded into said first syringe through said first bulk fluid container interface of said cassette and said first tubing set portion.

23. A method of delivering a medical fluid to a vasculature of a patient, said method comprising:
a. installing a cassette on a bulk fluid container holder module, wherein a multi-use tubing set extends from said cassette;
b. fluidly attaching said multi-use tubing set to an injection device;
c. fluidly interconnecting a first patient-specific tubing set to said multi-use tubing set;
d. fluidly connecting a first bulk fluid container to a first bulk fluid container fluid interface of said cassette;
e. actuating, after said installing, fluidly attaching, fluidly interconnecting, and fluidly connecting steps, a first valve of said cassette to place said first bulk fluid container in fluid communication with said multi-use tubing set; and
f. performing a fluid transfer sequence, wherein said fluid transfer sequence comprises:
retracting a plunger of said injection device while said first bulk fluid container is in fluid communication with said multi-use tubing set, resulting in fluid moving from said first bulk fluid container into a syringe of said injection device;
closing said first valve after said retracting step; and
advancing, after said closing step, said plunger to expel fluid from said syringe into said multi-use tubing set, through said first patient-specific tubing set, and into said vasculature of said patient.

24. The method of claim 23, further comprising fluidly connecting a second bulk fluid container to a second bulk fluid container fluid interface of said cassette.

25. The method of claim 24, wherein said first bulk fluid container comprises saline and said second bulk fluid container comprises contrast.

26. The method of claim 23, further comprising heating a fluid contained in said first bulk fluid container.

27. The method of claim 23, further comprising, before said actuating step, reading an identification member attached to said cassette.

28. The method of claim 27, wherein said reading said identification member attached to said cassette comprises reading an RFID tag.

29. The method of claim 23, further comprising, before said actuating step, reading an identification member attached to said first bulk fluid container.

30. The method of claim 29, wherein said reading said identification member attached to said first bulk fluid container comprises reading an RFID tag.

31. The method of claim 23, wherein said first bulk fluid container fluid interface comprises a vented spike mounted to said cassette, and wherein said fluidly connecting step comprises pressing said first bulk fluid container onto said vented spike.

32. The method of claim 23, further comprising:
disconnecting said first patient-specific tubing set from said multi-use tubing set after said performing step;
fluidly joining a second patient-specific tubing set to said multi-use tubing set after said disconnecting step; and
repeating said performing said fluid transfer sequence using said second patient-specific tubing set to deliver fluid into a vasculature of a second patient.

33. The method of claim 32, further comprising:
maintaining a position of said plunger between said disconnecting and fluidly joining steps; and
positioning, during said maintaining step, said first valve such that said first bulk fluid container is in fluid communication with said multi-use tubing set thereby preventing any pressure build up in said syringe.

34. The method of claim 32, wherein said disconnecting occurs at an interface of a female Luer connector of said multi-use tubing set and a first male Luer connector of said first patient-specific tubing set, wherein said joining occurs at an interface of said female Luer connector and a second male Luer connector of said second patient-specific tubing set, wherein said method further comprises cleaning said female Luer connector after said disconnecting step and prior to said joining step.

* * * * *